(12) United States Patent
Paakkanen et al.

(10) Patent No.: US 7,520,159 B2
(45) Date of Patent: Apr. 21, 2009

(54) GAS CHROMATOGRAPH

(75) Inventors: Heikki Paakkanen, Kuopio (FI); Mikko Utriainen, Mikkeli (FI)

(73) Assignee: Environics OY, Mikkeli (FI)

( * ) Notice: Subject to any disclaimer, the term of this patent is extended or adjusted under 35 U.S.C. 154(b) by 137 days.

(21) Appl. No.: 10/586,760

(22) PCT Filed: Jan. 21, 2005

(86) PCT No.: PCT/FI2005/000045

§ 371 (c)(1),
(2), (4) Date: Oct. 30, 2006

(87) PCT Pub. No.: WO2005/071395

PCT Pub. Date: Aug. 4, 2005

(65) Prior Publication Data

US 2007/0256474 A1 Nov. 8, 2007

(30) Foreign Application Priority Data

Jan. 23, 2004 (FI) .................................. 20040098

(51) Int. Cl.
*G01N 30/72* (2006.01)
(52) U.S. Cl. .................... 73/23.37; 73/23.35; 73/23.39
(58) Field of Classification Search ............... 73/23.35, 73/23.37, 23.39
See application file for complete search history.

(56) References Cited

U.S. PATENT DOCUMENTS 4,547,289 A * 10/1985 Okano et al. ................. 210/652
5,139,668 A * 8/1992 Pan et al. .................. 210/321.8
5,160,625 A 11/1992 Jönsson et al.
5,578,204 A 11/1996 Bartholmes et al.
5,856,616 A 1/1999 Maswadeh et al.
5,928,956 A 7/1999 Rotzsche et al.
6,270,674 B1 * 8/2001 Baurmeister et al. ........ 210/649

FOREIGN PATENT DOCUMENTS

EP 0 369 769 A2 5/1990
EP 1 203 953 A2 5/2002
JP 61-265567 A 11/1986

OTHER PUBLICATIONS

Ji, Z., et al., "Porous layer open-tubular capillary columns: preparations, applications and future directions", *Journal of Chromatography*, vol. A, 842, pp. 115-142, (1999).
Baumbach, J.I., et al., "Coupling of Multi-Capillary Columns with two Different Types of Ion Mobility Spectrometer", *International Journal for Ion Mobility Spectrometry*, vol. 3, No. 1, pp. 28-37, (2000).

* cited by examiner

*Primary Examiner*—Daniel S Larkin
(74) *Attorney, Agent, or Firm*—The Nath Law Group; Jerald L. Meyer; Jiaxiao Zhang

(57) ABSTRACT

The invention relates to a gas chromatograph for the analysis of gas samples. It has a feed arrangement for feeding the sample, an open tubular capillary column for separating the components of the sample, temperature control means for controlling the temperature of the column, and a detector for detecting the separated components of the sample. The efficiency has been improved and a convenient hand-held version has been made possible by constructing the column of a bundle of open tubular capillaries having a gas permeable wall comprising a polymer membrane. The invention also relates to the use of such a column together with a detector for identifying gaseous samples.

21 Claims, 2 Drawing Sheets

GAS CHROMATOGRAPH

FIELD OF THE INVENTION

The invention relates to a gas chromatograph for the analysis of a sample, having a feed arrangement for feeding the sample, an open tubular capillary column for separating the components of the sample, temperature control means for controlling the temperature of the column, and a detector for detecting the separated components of the sample, wherein said column comprises a bundle of open tubular capillaries.

BACKGROUND

The chemical state of a gas phase sample is formed by vaporized or gaseous chemical species mixed with an ambient medium, typically environmental air. Instead of air, the medium can be process gases or vacuum. The detector is used to detect and identify defined chemical species in the defined surrounding media.

Characteristic for a chemical detector is its capability to convert a chemical state to an electrical signal and transmit the signal for further processing. Typically it is aimed at performing both qualitative and quantitative determination of defined chemical species in a defined ambient medium. In that case, a technical concern is that the detector output is not completely specific, but possesses sensitivity to other chemical species than those aimed at. This behaviour is often referred as cross-sensitivity and typically leads to false positive identification.

Two fundamental ways to reduce the cross-sensitivity problem of the chemical detectors are (i) the development of more specific sensors (where the sensor is considered as the first part of a measuring chain converting the input variable into a signal suitable for measurement) or (ii) performing chemical separation before detection. Typical solutions for the latter case are using chromatography techniques or filtration or controlled adsorption-desorption techniques or applying sample preparation procedures including for example dissolution, phase separation, extraction, chemical derivatization and ion exchange. In the case of detecting the gas phase chemical state, and more preferably when detecting minor constituents in the environmental air by a portable detector, the sample preparation steps are less favoured as they are difficult to automatize, difficult to mobilize and also time consuming, and thus not suitable for fast real-time monitoring.

Of the remaining possibilities, chromatography is a well-known method in analytical chemistry for performing chemical separation. Gas chromatography (GC) is a method of choice for the separation of stable and volatile compounds as well as of gas phase samples. The method accomplishes chemical separation by partitioning the components of a mixture between a mobile gas phase and a stationary solid or liquid phase held on a solid support. In a fixed chromatographic system the retention time (which is the time passing when the sample travels from the inlet through the column to the detector) is constant for a particular analyte and, therefore, can be used to identify it. Thus, although chromatography is primarily a separation technique, it is possible to identify the separated compounds of a complex sample by their retention times. The process is carried out in a GC instrument consisting typically of a sample feed arrangement, a carrier gas and its flow controller unit(s), one or more columns inside a chamber (typically equipped with a thermostat), and one or more of said chemical detectors.

A crucial technical component of GC in respect to separation power and thus resolution of the analysis is the column. Two basic columns can be distinguished: (i) the packed column and (ii) the open tubular or so called capillary column. The packed columns are constructed from tubing of e.g. stainless steel, nickel or glass, inner diameters ranging typically from 1 mm to 10 mm. The columns are packed with an inert support powder, usually diatomaceous earth with an average internal pore diameter of 1-10 μm and a particle size of 100-200 μm. The second column type, the open tubular capillary column, has a narrow internal diameter of 10-1000 μm. It is typically constructed of fused silica (a very high purity glass) while the outer wall is protected by hard and tough polymer, like polyimide. Furthermore, they are characteristically of tubular shape with an unrestricted flow path in the middle of the column. The inner fused silica surface is chemically modified by various type of coatings or films which provide so called stationary phases with different polarity and thus selectivity for the separation process. The stationary phase can be a liquid layer or a thin film typically made of polymer such as polysiloxane, silicone or polyamide, optionally functionalised in different ways. Factors such as chemistry, microstructure, morphology and thickness of the stationary phase film influence the total separation power of the column.

Of the column types, the open tubular capillary column is favoured in analytical chemistry due to its better separation power per total analysis time, better long-term stability and higher quality due to a more reproducible manufacturing process.

The use of open tubular GC capillary tubes in combination with various portable chemical detectors is well-known in the art as can be concluded from the following citations: U.S. Pat. No. 5,114,439 and U.S. Pat. No. 5,856,616 disclose the use of compact sized and low power consuming GC columns for portable applications. Also WO9941601 discloses the use of a combined specific sampling system and a low power consuming GC column. Furthermore, U.S. Pat. No. 4,888,295 discloses the use of "a commercially available" GC column in combination with detector formed by an array of electrochemical sensors (CPS), and U.S. Pat. No. 6,354,160 discloses the use of a GC column in parallel with SAW-sensor based detectors, where the open tubular GC columns may also be those formed on silicon wafers.

Applying the GC method in portable devices, and preferably in hand-held size devices, requires devices which are low-power consuming, light and compact sized and have a fast detection while still maintaining a high resolution through high separation power. So far, the improvements of portable devices have mainly concerned the use of high column temperatures as well as improvements in temperature control and in the construction of the heating system. Furthermore, prior art improvements have concerned modifications of the carrier gas flow as well as design of special sampling and detecting systems.

Other ways for improving the GC method's suitability to portable applications have included shorter columns and columns with smaller inner diameter in order to enhance the efficiency and the speed of the analyses. However, these improvements will lead to reduced separation or alternatively, they will reduce the sample volume and increase significantly the power requirement and thus the cost and dimensions of the pump due to increased pressure drop in the column. The drawbacks of using a low sample volume is that it typically leads to weakened response by the detector and increased sensitivity to local variations in the sample leading thus poorer accuracy in retention time. Also controlling small volumes of fluid can be a technically demanding as well as an expensive solution.

These drawbacks have been overcome by using a column which comprises a bundle of open tubular capillaries. See e.g. Baumbach et al. (1997) and Baumbach et al. (2000).

Such columns are manufactured and/or sold by only a few companies, namely, Alltech Associates Inc. (Deerfield, Ill., USA), ChemSpace s.r.o (Pardubice, Czech Republic), Sibertech (Novosibirsk, Russia). The advantages of multicapillary columns are that they provide short retention times and thus fast detection times at sufficiently high resolution and separation capability. Furthermore, they retain high efficiency over a wide range of carrier gas flow rates and, thus, compared to conventional single capillary columns, they can be operated with larger sampling volumes that are easy to inject and detect.

Thus, the properties of the claimed multicapillary column makes it ideal for a hand-portable gas chromatograph.

However, since multicapillary columns are typically formed by hundreds of single capillary columns, it is difficult to obtain uniform thermal distribution with low power consumption for the sufficiently massive bundles, which reduces the accuracy of the GC analysis.

Even though multicapillary GC columns facilitate much higher sampling flow rate (or carrier gas flow rate) through the column than a single open tubular GC column, the compatible gas flow rate for conventional multicapillary columns still remains below 300 ml/min. In some detector types this flow rate can be still far too low. Such detector is, for example, a hyphenated multisensor-ion mobility spectrometer designed for detecting gaseous chemical species in the environmental air by direct flow-through principle as described in references WO9416320 and Utriainen et al. (2003).

The detector employs a special type of ion mobility spectrometer (IMS) referred to as aspiration condenser type or open loop type IMS combined with other sensors such as semiconductor gas sensors, temperature and humidity sensors. The detector is manufactured for hand-held and portable chemical detector devices under trademarks such as ChemPro100, M90-D1-C (Environics Oy, Mikkeli, Finland) and MultiIMS (Dräger Safety, Lubeck, Germany). Further characteristic for this detector is that it employs continuous, typically 800-3500 ml/min, preferably 1000-2000 ml/min flow-through providing thus good statistical sampling accuracy and fast response and recovery times which are all essential features especially when aiming at to provide reliable early warning of the presence of toxic substances in the air. Characteristic feature for this detector is also that the sensitivity depends on flow rate in such manner that the higher flow rate is favored. Other characteristic features of the detector are the sensitivity to rapid flow (and pressure) changes and rapid and large humidity and temperature changes.

SUMMARY OF THE INVENTION

Thus, a need for further improvement exists. This need has in the invention been satisfied so that in the multicapillary column used according to the invention, the open tubular capillaries have gas permeable walls comprising a polymer membrane. The polymer membrane wall selectively delays some and lets through some components of the streaming sample gas and thus further improves the separation of the column. The column can be made shorter and less pressure is needed to pump the gas.

According to a preferred embodiment, the present invention employs a bundle of such hollow fiber membrane capillaries as a multicapillary GC column to perform chemical separation in a portable chemical detector to improve the detector's chemical specificity. The portable chemical detector is most preferably part of a hand-held analyzator. The hollow fiber membrane bundles have before been extensively used in industrial gas separation processes, industrial gas dryers, on-site gas generators as well as in dialysis filters for separating components in liquid phase. The wide range of applications of the hollow fiber membranes provides high manufacturing volumes and that way access to low cost components for niche applications like for the claimed chemical detection.

A purely polymer-based structure of the membrane capillaries provide lower processing and material costs compared to conventional GC capillary columns of used silica, and that way also more cost-efficient solution.

The hollow fiber capillary membrane walls are characteristically permeable, at least to low molecular weight gases, while conventional fused silica based GC columns are not. Also, the materials used for the present hollow fiber manufacturing are characteristically polymers, which are, furthermore, characteristically suitable for low temperature synthetic fiber spinning processes. Examples of such materials are polyolefins, polyamide and polyester as well as less common materials in fiber spinning such as polysulfone and cellulose acetate. Also so called bicomponent fibers are suitable for hollow fiber capillary membranes, meaning formation of designed structure of two polymer materials. Typical example is a layered capillary where inner and outer wall are constructed of different polymers in one process or in several process steps. The inner wall is according to one embodiment a membrane polymer and the outer wall a porous polymer supporting the membrane polymer. Thus, the wall as a whole is selectively permeable.

The bundle of hollow fibres is typically elastic and easily handled in packaging process. Due to its common use as membranes, the outer side of fiber takes part in the separation process and is typically thus left without any interstitial material which allows fluid stream on both sides. This assembly is advantageous for obtaining homogeneous thermal distribution due to possibility to use fluids for thermostatting of bundles. Simple and low power consuming thermostatting possibility allows reducing thermal effects on the detector as well as to improve accuracy for the chemical identification.

Further advantage of the invention is that when using a hollow fiber membrane bundle, initially designed to an industrial dryer, a simultaneous and selective elimination of water and other analytically uninteresting small molecular substances from the sample can be obtained. Moisture is considered as an interferent for chemical detection, in general, and can be especially a concern in the case of high volume flow-through detectors and ion mobility spectrometers. Similarly, other types of gas permeation selective bundles of hollow fiber capillary membranes are useful to perform simultaneously filtration based chemical separation with the chromatographic separation. Namely, as discussed above, the filtration can be considered as an alternative approach to improve chemical separation power of the chemical detectors, in general.

The dimensions and number of the capillaries forming the bundle column used according to the invention can vary widely. Typically, there are between 10 and 10000 pieces of open tubular membrane capillaries in the bundle. Each capillary typically has a length of 10 to 100 cm and an inner diameter of 10 to 1000 μm. Preferably, the bundle contains 100 to 4000 pieces of said open tubular capillaries. The inner diameter of the tubular capillaries is preferably from 50 to 1000 μm.

Generally, the bundle consists of said open tubular capillaries in essentially straight and parallel formation having open space between them. The unwanted small molecules such as water migrate out of the capillaries into the open space and therefrom to a vent of the system. When constructing the column and/or bundle used by the invention, a holder or cap typically holds together said capillaries so that only gas from within the capillaries reaches the detector. A cover may surround said bundle.

In the gas chromatograph according to the invention, the used temperature control means preferably include a heating medium arranged to flow through said open space between said capillaries. The construction resembles a heat exchanger and excellently solves the heat transfer problems usually connected with small portable gas chromatographs. For such heating problems, see e.g. U.S. Pat. No. 5,114,439.

Said temperature control means also preferably include the above-mentioned cover which is made of heat insulating material and has inlet and outlet openings for allowing the heating medium to flow through the open space between the capillaries. When using a heating medium which streams past the capillaries, the temperature control means further include a thermostat heater for controlling the temperature of said heating medium and preferably a pump and a hose or tube. The pump conveys the heating medium between the thermostat heater and the bundle, further through the open space between the capillaries and preferably back to the heater.

The feed arrangement of the claimed gas chromatograph typically comprises an absorbing filter for generating a clean air reference for the chromatographic system. Further, said feed arrangement comprises a gas inlet for letting the gas sample into said column. There may also be a valve for directing the sample to the column, alternatively directly or through said filter, and another valve for directing the sample, alternative through the column or directly to the detector.

In the claimed gas chromatograph, said detector typically comprises an ion mobility spectrometer IMS. Preferably, the IMS is a hyphenated multisensor IMS designed for direct flow-through of the sample.

The invention also relates to a method for analyzing a sample by means of the above described gas chromatograph. Typically, the sample is fed to the column with a speed of 100 to 100000 ml/min. Preferably, the speed is 100 to 3500 ml/min and most preferably 1000 to 2000 ml/min. It is advantageous to feed the sample continuously to the detector. As stated above, the system can be packed into a small space and is therefore suitable as a hand-held analyzer. Thus, the claimed method has the feature that the gas chromatograph is carried by hand to and/or from the spot of analysis.

The idea of the invention is to combine an open tube capillary bundle with a detector. The bundle effectively separates the components of the sample to be analyzed and the detector detects them. Thus, the invention also relates to the use of a bundle containing open tubular capillaries having a wall of a gas permeable polymer membrane together with a detector for separating and analyzing a gas sample.

Said bundle may form a dialysis filter, whereby the inner capillary wall preferably has a high specific surface area. The bundle may also form an industrial dryer, which is its original field of use. In that case, the inner wall of the capillaries is smooth and has a low permeability. Most preferably, the bundle forms the column and the detector forms a detector, of a gas chromatograph. The properties of such a gas chromatograph are given above. Because of its efficiency, the gas chromatograph is preferably a hand-held gas analyzer.

Optimally, a hollow fiber capillary membrane based GC unit combined with the chemical detector according to the invention can provide sufficient chemical separation power to improve significantly the cross-sensitivity problem. The device can be operated by a high flow rate, without any notable pressure or flow rate changes and can stabilize rapid humidity and temperature changes. Furthermore, it is sufficiently small, low weight and low power consuming device to be used in mobile applications and low cost device for facilitating commercial success.

BRIEF DESCRIPTION OF THE DRAWINGS

The invention is illuminated in the enclosed FIGS., in which:

FIG. 1 (*b*) shows the air flow when the claimed system is in alarmed position;

FIG. 1 (*c*) shows the air flow when the claimed system receives a sample;

FIG. 2 (*b*) shows the longitudinal section of an open capillary membrane bundle used as a GC column according to the invention;

FIG. 2 (*c*) shows the cross-section of said open capillary membrane bundle.

DETAILED DESCRIPTION OF THE INVENTION

Figure 1A:
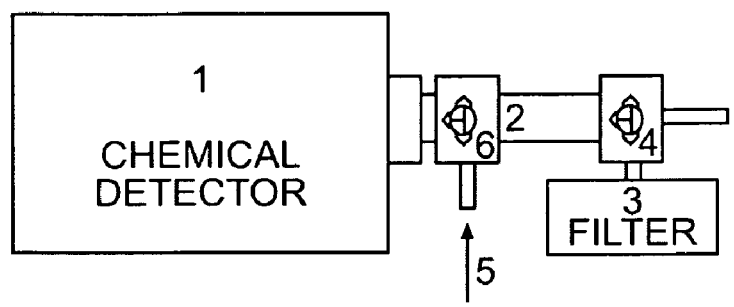
FIG. 1 (*a*) shows the air flow when the claimed system is in non-alarmed position.
Figure 1B:
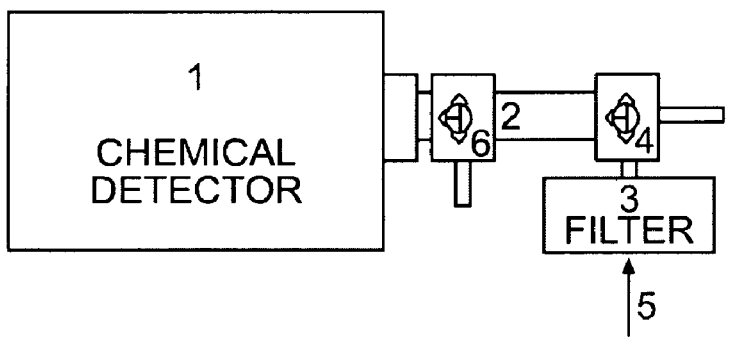
Figure 1C:
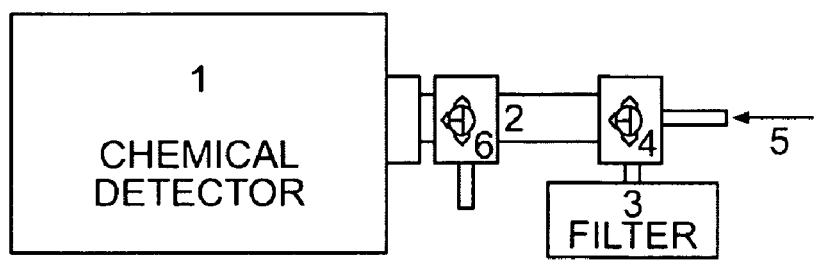

FIG. 1 describes one preferred embodiment of using the hollow fiber capillary membrane bundle (2) as a GC column combined with a chemical detector (1). The sampling arrangement contains a valve (4), a vapor adsorbing filter (3), a gas inlet (5) and an optional additional valve (6). The position of the valve (4) determines whether the sample flows through the filter, see FIG. 1 (*b*), or directly, see FIG. 1 (*c*), to the hollow fiber bundle based multicapillary GC column (2). The moment of switching the valve from the position shown in FIG. 1 (*b*) to the position shown in FIG. 1 (*c*) represents the point t=0 of the retention time.

Another preferred embodiment, also shown in FIG. 1, involves the additional valve (6) which is used to control whether the hollow fiber bundle based GC column is in use the positions shown in FIGS. 1 (*b*) and 1 (*c*)) or not the position shown in FIG. 1 (*a*)). A faster response time is possible when a hollow fiber bundle is not used the position shown in FIG. 1 (*a*)), but a more specific identification with less cross-sensitivity is possible when using the bundle shown in FIGS. 1 (*b*) and (*c*)).

Figure 2A:
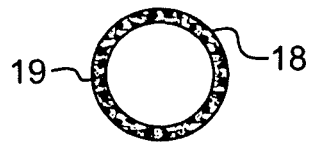
FIG. 2 (*a*) shows the cross-section of a single open tubular capillary used in the claimed gas chromatograph.
Figure 2C:
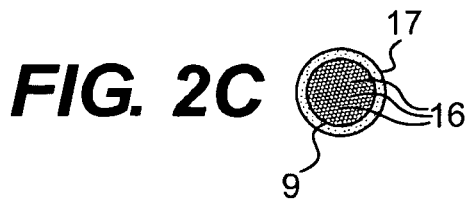
Figure 2B:
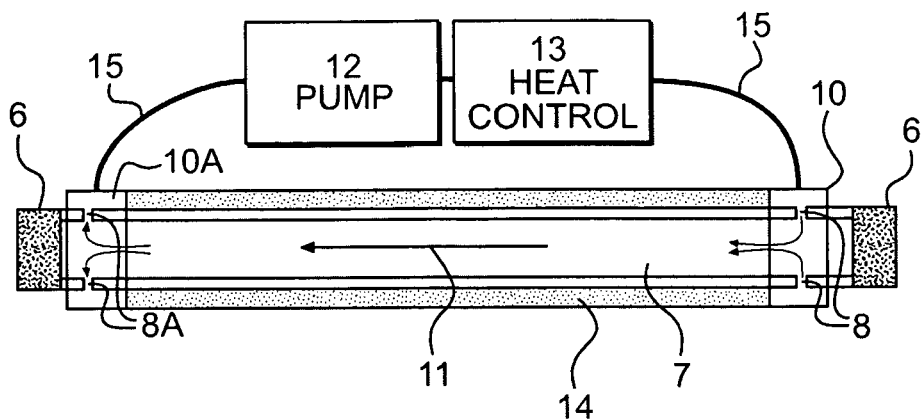

FIG. 2(*a*), shows the cross-section of a single hollow fibre used in a membrane bundle according to the invention. The wall consists of an outer layer of support material (18) and an inner active membrane layer (19). FIG. 2 (*b*) shows a longitudinal section and FIG. 2 (*c*) shows a cross-section of a preferred embodiment of a temperature regulation arrangement for the hollow fiber capillary membrane bundle used as a GC column. The bundle is packed in an airtight closed package where the cover (14) is made of heat insulator material. Controllably heated and thermostated (13) fluid (liquid or gas) is circulated (11) through the package by means of a pump (12) and a tube (15), thus forming an interstitial medium (7) between the capillaries (16). In one preferred embodiment the interstitial medium fluid (7) is glycerol or industrial coolant solution. In another preferred embodiment the interstitial medium fluid (7) is air.

Another preferred embodiment employs a similar construction as shown in FIG. 2, but in this case, the system can either have heater (13) or not. In this preferred embodiment the interstitial medium fluid (7) is air, with a primary role for purging the system. Air is pumped only into the inlet (10) opening (8) and out through the outlet (10a) opening (8a) (i.e. the heating media tube 15 is missing).

In all cases, the interstitial medium fluid (7) is isolated from the sample gas by a stopper construction at the tube end (6). In the preferred embodiment the filling material (9) seen at the tube end (cross section view) fills only the space between capillaries and also bonds the capillaries together. In one preferred embodiment the filling material (9) is epoxy polymer.

In one preferred embodiment, the bundle (2) is a high-selective type hollow fiber capillary membrane bundle from industrial dryer sold under trademarks as Drypoint (Beko), MF-Dryer (CKD, Wilkinson), SF-Serie (Whatman, Balston), Sunsep (Zander, SMC), VarioDry (Ultrafilter) and Porous Media (Norgren). In this case, the structure of the capillary wall is shown in FIG. 2a and consists characteristically of an actual hollow fiber as a porous support (18) and an active dense layer (membrane) (19) covering the inner surface.

In one preferred embodiment the detector (1) is a hyphenated multisensor-IMS sold under trademarks as ChemPro100 (Environics), M90-D1-C (Environics), Multi-IMS (Dräger) or any other IMS based detector.

EXAMPLES

The following examples illustrate, but do not limit, the basic features of the present invention.

The arrangement is similar as those presented in FIG. 1 and FIG. 2. The bundle of hollow fiber membrane capillaries originates from a membrane dryer (Drypoint Beko). The detector is ChemPro100 (Environics) using 1 l/min flow rate.

The zero time (retention time=0) is determined by switching the valve (4) from the position shown in FIG. 1 (b) to the position shown in FIG. 1 (c).

Figure 3:
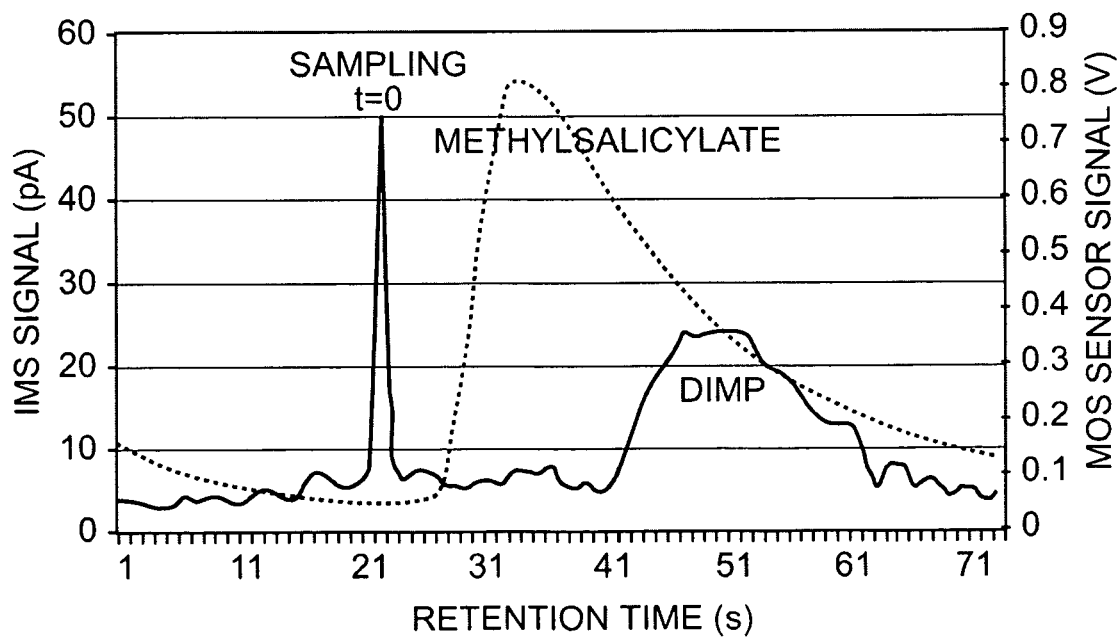
FIG. 3 shows the result of feeding mixtures of methyl salicylate (MeS) and di-isopropyl methyl phosphonate (DIMP) (1% DIMP and 99% MeS) through a bundle of hollow fiber membranes to a detector according to the invention.

FIG. 3 shows a result of feeding mixtures of methyl salicylate (MeS) and di-isopropyl methyl phosphonate (DIMP) (1% DIMP and 99% MeS) through a bundle of hollow fiber membranes to the detector.

The detector sucks air through a filter and measure a clean background signal. The valve (4) was switched to the position shown in FIG. 1 (c) and the sample was introduced at the same time. After three seconds the valve 4 was switched to the position shown in FIG. 1 (b). This procedure introduces a sample bolus into the fibers between clean air.

Within about forty seconds, both chemicals have eluted through the column and detected selectively by ion mobility spectrometry (DIMP) and by metal oxide gas sensor (MeS). If in case the sample had been introduced through valve 6 as in FIG. 1 (a), there would be no time delay between the signals.

The present invention concerns an apparatus which is used as a chemical detector, and more preferably as an additional device which performs chemical separation and is combined with any chemical detector. The invention improves the chemical specificity of chemical detectors, consists of low cost components and facilitates rugged design. The invention is especially useful when it is used for identifying the presence of chemical warfare agents and other toxic and flammable gases and vapors in applications such as military, industrial or personal protection or industrial or environmental hygiene or industrial process control.

REFERENCES

U.S. Pat. No. 5,114,439: Hail, M. E. and Yost, R. A., Direct resistive heating and temperature measurement of metal-clad capillary columns in gas chromatography and related separation techniques.
U.S. Pat. No. 4,888,295: Solomon, Z. and Stetter, J., Portable System and Method Combining Chromatography and Array of Electrochemical Sensors.
U.S. Pat. No. 5,856,616 Waleed, M. M. and Snyder, P. A., Hand-held temperature programmable modular gas chromatograph.
WO9941601 Thekkadath, G. and Haley, L. V., Hand-held detection system using GC/IMS.
U.S. Pat. No. 6,134,944 Koo, J. C. and Yu, C. M., System and Method for preconcentrating, identifying and quantifying chemical and biological substances
Utriainen, M., Paakkanen, H. and Kärpänoja, E., Combining miniaturized ion mobility spectrometer and metal oxide gas sensor for the fast detection of toxic chemical vapors, *Sens. Actuators B* 93 (2003) 17-24.
WO9416320 Paakkanen, H., Kärpänoja, E., Kättö, T., Karhapää, T., Oinonen, A. and Salmi, H., Method and equipment for definition of foreign matter contents in gases.
Baumbach, J. I., Eiceman, G. A., Klockow, D., Sielemann, S., von Irmer, A., Exploration of a multicapillary column for use in elevated speed chromatography, Int. J. Env. Anal. Chem. 66(1997)225-239.
Baumbach, J. I., Sielemann, S., Pilzecker, P., Coupling of multi-capillary columns with two different types of ion mobility spectrometer, Int. J. for Ion Mobility Spectometry 3(2000)28-37.

The invention claimed is:

1. Gas chromatograph for the analysis of a sample, having a feed arrangement for feeding the sample, an open tubular capillary column for separating the components of the sample, temperature control means for controlling the temperature of the column, and a detector for detecting the separated components of the sample, wherein said column comprises a bundle of open tubular capillaries, characterized in that said open tubular capillaries have gas permeable walls comprising a polymer membrane.

2. Gas chromatograph according to claim 1, characterized in that the gas chromatograph is a hand-held portable gas chromatograph.

3. Gas chromatograph according to claim 1 characterized in that said walls have an inner layer of a selectively gas permeable polymer membrane and an outer layer of a porous polymer support.

4. Gas chromatograph according to claim 1 characterized in that said bundle has between 10 and 10000 pieces of open tubular capillaries.

5. Gas chromatograph according to claim 1, characterized in that said open tubular capillaries have a length of 10 to 100 cm and an inner diameter of 10 to 1000 μm.

6. Gas chromatograph according to claim 1, characterized in that said bundle contains 100 to 4000 pieces of said open tubular capillaries.

7. Gas chromatograph according to claim 1, characterized in that the inner diameter of the tubular capillaries is from 50 to 1000 μm.

8. Gas chromatograph according to claim 1, characterized in that said open tubular capillaries have open space between them.

9. Gas chromatograph according to claim 8, characterized in that said temperature control means include a heating medium arranged to flow through said open space between said capillaries.

10. Gas chromatograph according to claim 9, characterized in that said temperature control means include said cover which is made of heat insulating material and has inlet and outlet openings for allowing said heating medium to flow through said open space between said capillaries.

11. Gas chromatograph according to claim 9, characterized in that said temperature control means include a thermostat heater for controlling the temperature of said heating medium.

12. Gas chromatograph according to claim 11, characterized in that said temperature control means include a pump and a hose or tube for pumping and conveying said heating medium between said thermostat heater and the open space between said capillaries.

13. Gas chromatograph according to claim 1, characterized in that said column has a cover surrounding said bundle.

14. Gas chromatograph according to claim 1, characterized in that said feed arrangement comprises a filter for absorbing vapour from the sample before it enters the column.

15. Gas chromatograph according to claim 14, characterized in that said feed arrangement comprises a valve for directly directing the sample to said column (2) or alternatively through said filter.

16. Gas chromatograph according to claim 1, characterized in that said feed arrangement comprises a gas inlet for letting the sample into said column.

17. Gas chromatograph according to claim 1, characterized in that said feed arrangement comprises a valve for directing the sample through said column or alternatively directly to said detector.

18. Gas chromatograph according to claim 1, characterized in that said detector is an ion mobility spectrometer (IMS).

19. Gas chromatograph according to claim 18, characterized in that the ion mobility spectrometer is a hyphenated multisensor ion mobility spectrometer designed for direct flow-through of the sample.

20. Gas chromatograph according to claim 19, characterized in that said detector employs semiconductor sensors, electroacoustic gas sensors or sensor arrays thereof, or humidity and temperature sensors, or a combination of any of those, in which case at least one sensor is said ion mobility spectrometer.

21. Gas chromatograph according to claim 1, characterized in that said gas chromatograph is a portable and/or hand-held gas analyzer.

* * * * *